(12) United States Patent
Suga et al.

(10) Patent No.: US 7,930,770 B2
(45) Date of Patent: Apr. 26, 2011

(54) PANTY

(75) Inventors: Ayami Suga, Kagawa (JP); Shinobu Fujikawa, Kagawa (JP); Hideki Kondo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 77 days.

(21) Appl. No.: 12/180,156

(22) Filed: Jul. 25, 2008

(65) Prior Publication Data

US 2008/0282452 A1 Nov. 20, 2008

Related U.S. Application Data

(60) Division of application No. 11/075,399, filed on Mar. 7, 2005, now abandoned, which is a continuation of application No. PCT/JP2004/002088, filed on Feb. 23, 2004.

(30) Foreign Application Priority Data

Feb. 25, 2003 (JP) ................................. 2003-048105

(51) Int. Cl.
*A41B 9/04* (2006.01)
*A41B 9/00* (2006.01)

(52) U.S. Cl. ............... 2/406; 2/73; 2/109; 2/113; 2/329; 2/400; 2/401; 2/402

(58) Field of Classification Search .................. 604/402; 2/401, 406, 73, 109, 113, 329, 400, 402
See application file for complete search history.

(56) References Cited

U.S. PATENT DOCUMENTS

| 2,056,639 | A |   | 10/1936 | Wipperman |
| 2,125,482 | A | * | 8/1938 | Barnes ........................... 450/132 |
| 2,171,913 | A |   | 9/1939 | Bullinger |
| 2,344,374 | A |   | 3/1944 | Stephens |
| 3,098,484 | A | * | 7/1963 | Younger ........................ 604/396 |
| 3,608,551 | A | * | 9/1971 | Seijo ............................. 604/396 |

(Continued)

FOREIGN PATENT DOCUMENTS

CN 1285727 2/2001

(Continued)

OTHER PUBLICATIONS

Office Action issued to co-pending U.S. Appl. No. 12/180,011 mailed Jun. 17, 2010, 11 pages.

(Continued)

*Primary Examiner* — Tatyana Zalukaeva
*Assistant Examiner* — Ginger T Chapman
(74) *Attorney, Agent, or Firm* — Brinks Hofer Gilson & Lione

(57) ABSTRACT

The invention provides a panty realizing easy fit of a sanitary napkin for night use to a crotch portion, preventing the napkin from shifting out of position, alleviating digging into the crotch portion, and thus being comfortable to wear without giving feeling of constriction to the wearer. The panty includes a front part, a back part, a crotch part provided so as to bridge between the front part and the back part, a slightly elastic member is provided at the substantially center area of the back part, a highly elastic member is provided from a back parts lifting member to the entire area of the front part except for the waist hold part, a fixing member is provided on the substantially center area of the front part, a crotch lifting member is provided at the substantially center area of the crotch part.

8 Claims, 11 Drawing Sheets

U.S. PATENT DOCUMENTS

| | | | |
|---|---|---|---|
| 3,687,141 A * | 8/1972 | Matsuda | 604/396 |
| 5,546,607 A | 8/1996 | Roberts | |
| 5,787,732 A * | 8/1998 | Perron et al. | 66/177 |
| 5,855,573 A * | 1/1999 | Johansson | 604/385.17 |
| 6,539,555 B2 * | 4/2003 | Suga et al. | 2/406 |
| 6,613,034 B2 | 9/2003 | Nozaki et al. | |
| 6,616,649 B1 | 9/2003 | Ismail | |
| 6,626,883 B2 * | 9/2003 | Wada et al. | 604/396 |
| 6,807,685 B1 * | 10/2004 | Hasegawa et al. | 2/406 |
| 6,848,121 B1 * | 2/2005 | Halid | 2/400 |
| 2001/0020158 A1 | 9/2001 | Nozaki et al. | |

FOREIGN PATENT DOCUMENTS

| | | |
|---|---|---|
| EP | 1 132 070 A2 | 9/2001 |
| EP | 1 166 738 A2 | 1/2002 |
| JP | 02-114988 | 4/1990 |
| JP | 3063342 U | 8/1999 |
| JP | 2001-245929 A | 9/2001 |
| JP | 2001-276129 A | 10/2001 |
| JP | 2001-276130 A | 10/2001 |
| JP | 2001-522698 | 11/2001 |
| JP | 2002-000660 A | 1/2002 |
| JP | 2002-017782 A | 1/2002 |
| JP | 2002-095699 A | 4/2002 |
| JP | 2002-095700 A | 4/2002 |
| WO | 99/25298 A1 | 5/1999 |
| WO | 99/25299 A1 | 5/1999 |
| WO | 9925298 | 5/1999 |
| WO | WO-99/25289 | 5/1999 |
| WO | 01/01911 A1 | 1/2001 |

OTHER PUBLICATIONS

Notice of Allowance issued to co-pending U.S. Appl. No. 12/180,011 mailed Jan. 21, 2011, 10 pages.

* cited by examiner

PANTY

CROSS-REFERENCE TO RELATED APPLICATIONS

This is a divisional of U.S. patent application Ser. No. 11/075,399 filed Mar. 7, 2005 which is a continuation application of International Application No. PCT/JP2004/002088 filed on Feb. 23, 2004 and published on Sep. 10, 2004 as International Publication Number WO 2004/075801 in English, the entire contents of which is incorporated herein by reference. The International Application No. PCT/JP2004/002088 is based upon and claims the benefit of priority from Japanese Patent application No. 2003-048105 filed on Feb. 25, 2003, the entire contents of which is incorporated herein by reference.

FIELD OF THE INVENTION

The present invention relates to a panty for fitting a sanitary napkin on a crotch part and, particularly to a panty which can firmly hold the thick sanitary napkin for night use to prevent shifting out of position, is excellent in fitting property to the body, and hardly cause uncomfortable feeling for constraining of wearer's body.

RELATED ART

A panty is required to certainly and firmly retain a sanitary napkin attached to the crotch part thereof, to prevent the sanitary napkin from shifting out of position at the crotch part, and in addition, and to give a comfortable feeling to the wearer by alleviating digging into a crotch portion of the body.

As a panty of this type, a panty that has a section having a large tensile load bearing capacity in a center area between a front part and a back part, a crotch part positioned between the front part and the back part and joining the front part to the back part, and a pair of elastic openings for legs is disclosed (JP-2001-522958A). This panty has a longitudinal stretch control member disposed in the crotch region and stretch control members which are disposed in both the front part and the back part and extend from the longitudinal stretch control member to a waist band. The inventors of the present invention provided a comfortable panty which can easily fit the sanitary napkin to the crotch part preventing the sanitary napkin from digging into the crotch portion (JP-A-2002-660). This panty includes a waist band around the waist opening part and leg bands around the leg openings, respectively, and a crotch part intended to be used for a part to attach a sanitary napkin. And the panty is characterized in that the dimensional ratio between the center length from the crotch part to the waist opening part and the side length from the leg opening to the waist opening part, as taking that the center height length is 100, is in the range from 80 to 200 in the side height length when the dimensions are measured in a three-dimensional shaped condition as worn and an elastic lifting member is provided from the crotch part to the waist opening part in a back part.

However, according to the panty disclosed in JP-T-2001-522958, although the sanitary napkin placed on the crotch area can be fitted tightly to the body by the stretch control member, since the stretch control member is provided as a narrow strip, a force concentrates on one linear point, and thus the panty may dig into the body in the worn condition. In addition, the sanitary napkin may be bent at the center to form an upward projection, and thus the top of the bent may cause uncomfortable feeling to the wearer's body.

Moreover since two elastic leg openings are formed by stitching the front part and the back part together, the stitched portion extends at the center of the crotch part so as to connect the two leg openings. Therefore, when a sanitary napkin is attached to the panty, there is no base which can stably hold the sanitary napkin, and consequently, the problem may arise with regard to leakage due to the sanitary napkin kinked into a narrow shape or the adhesive section of the sanitary napkin peeled off the body of the panty.

According to the panty disclosed in JP-A-2002-660, the elastic lifting member provided on the back part extends in the longitudinal direction and generates a resilient contractive force. This resilient contractive force works substantially linearly along the medulla spinalis and then along the gluteal cleft and the crotch portion at the center of the back part. Therefore, a large lifting force in the for-and-aft direction is generated at the crotch part and thus the sanitary napkin on the crotch part is pressed to the ostium vagina.

This panty has a structure such that the elastic lifting member provided on the back part extends in the longitudinal direction and thus generates an elastic lifting force for fitting the sanitary napkin to the body. However, since the elastic lifting member is disposed on the back part and the front part is formed of a sufficiently elastic cloth, when the thick sanitary napkin for night use is attached to the panty, the sanitary napkin can not filled to the hip or the crotch portion because the elastic lifting member sprawls due to the thickness and high rigidity of the sanitary napkin and thus does not adequately exercise the force to push the sanitary napkin even when the sanitary napkin is lifted by the elastic lifting member disposed on the back part to fit it to the body.

Therefore, a gap is generated between the sanitary napkin and the body, and thus menstrual blood may flow down along the back sides and leak from the sanitary napkin. In addition, the problem that the menstrual blood might spread out through the gap and increases in the area of the skin coming into contact with menstrual blood, which gives a high burden to the skin, and may lead to irritation of the skin.

If the body is constricted, for example, by a tight girdle for preventing shifting out or kinking of the sanitary napkin when the wearer moves unconsciously during sleep, it may cause swelling or hematogenous disorder due to tightness, which gives significant stress to the body.

Therefore, a panty having a structure which does not constrict the entire body, but can press and fit only the necessary portion of the sanitary napkin to the body is desirable.

SUMMARY OF THE INVENTION

An object of the present invention is to provide a panty which can easily fit the thick sanitary napkin for night use to the crotch portion or the gluteal cleft, to prevent from shifting out of position, to prevent from digging into the crotch portion, and to provide a comfortable feeling without giving an uncomfortable feeling of constriction to the wearer.

Focusing on such problems in the related arts, the present invention provides a panty which is formed by providing a highly elastic member made of a highly elasticated material, and a slightly elastic member made of a slightly elasticated material, and has a crotch part provided so as to bridge the front part with the back part. The slightly elastic member is provided in a center area of the back part ranging from a rear end of the crotch part to a waist hold part. A longitudinal elastic coefficient of the slightly elastic member is set to be larger than a longitudinal elastic coefficient of the highly elastic member covering a hip and a belly around the center area. A napkin lifting part stitched the slightly elastic member of the back part is provided in a middle of the crotch part, and a longitudinal elastic coefficient of which is set to be larger than a longitudinal elastic coefficient of a crotch cloth constituting the crotch part covering the crotch portion therearound. With structures mentioned above, the invention was completed and the problems described above can be solved.

More specifically, the present invention provides:

(1) A panty formed by providing a highly elastic member made of a highly elasticated material and a slightly elastic member made of a slightly elasticated material, comprising: a front part, a back part, a crotch part provided so as to bridge between the front part and the back part, a waist opening part provided in an upper edge of the front part and an upper edge of the back part, and a pair of leg openings provided below both side edges of the front part and both side edges of the back part; wherein a band-shaped area provided in a substantially center area of the back part from the crotch part to the waist opening part is formed of the slightly elastic member.

According to the present invention, when the panty is pulled upward for being worn, the slightly elastic member allocated in the band-shape area provided from the crotch part to the waist part works to pull the crotch part connected thereto without extension. Accordingly, the sanitary napkin attached on the crotch part is pulled up and fitted to the crotch portion or the gluteal cleft of the body, whereby a gap is hardly generated between the sanitary napkin and the body and thus leakage of menstrual blood is prevented. Since the panty is made up of the highly elastic member which is highly elasticated, it is comfortable to wear without giving uncomfortable feeling of constriction all over the wearer's body as does with the girdle. Since the crotch part, being provided so as to bridge between the front part and the back part, is positioned around the pubic bone and the portion backward of the anal when the panty is worn, and thus the sanitary napkin can be stably attached to the crotch part when the wearer wears the panty with the sanitary napkin attached to the crotch part, and thus the sanitary napkin is prevented from kinking, thereby avoiding the risk of leakage of menstrual blood.

The front part here means the front portion of the panty body which covers the belly, and the back part represents the back portion of the panty body which covers the back side of the waist. The panty body means the portion which covers the waist portion of the body. The term "the crotch part is provided so as to bridge between the front part and the back part" means that the crotch part is formed by connecting the crotch cloth to the front part and the back part by stitching or the like, not by connecting the front part directly to the back part.

(2) The panty according to (1), wherein a longitudinal elastic coefficient of the slightly elastic member is larger than a longitudinal elastic coefficient of the highly elastic member.

According to the present invention, when the wearer attaches the sanitary napkin to a napkin fitting cloth and pulls the panty upward to wear, the slightly elastic member is pulled upward with the portion stitched between the crotch part and the slightly elastic member being a supporting point. Then, the force to pull up the slightly elastic member works as a force to pull the crotch part upward and as a force to suspend the sanitary napkin for night use attached to the napkin fitting cloth. In this case, since the longitudinal elastic coefficient of the slightly elastic member is larger than that of the highly elastic member disposed around the slightly elastic member, the force to suspend the sanitary napkin works effectively as a force to pull up the crotch part connected to the slightly elastic member and also the sanitary napkin attached to the crotch part. Therefore, unlike the panty having elasticity at the center area of the back part as in the related art which does not exert sufficient force to pull up the sanitary napkin with only the center area of the back part being extended even when the wearer pulls up the panty by holding the waist opening part, the panty according to the present invention can easily fit the thick sanitary napkin for night use to the crotch portion or to the gluteal cleft.

Preferably, the longitudinal elastic coefficient of this slightly elastic member ranges approximately between 10 N and 60 N, and more preferably, between 20 N and 50 N. When the elastic coefficient is smaller than 10 N, a force to suspend the sanitary napkin is not sufficient and hence does not effectively work as a force to suspend the sanitary napkin. In this case, when the wearer pulls up the panty, the slightly elastic member extends too much, and thus the force exerted by the wearer does not work effectively as a force to pull up the sanitary napkin. The elastic coefficient larger than 60 N is not preferable because a pulling up force larger than a force required for fitting the sanitary napkin is liable to be generated, and consequently, the sanitary napkin digs into the body more than necessary, which may cause uncomfortable feeling or pain. For example, material which is not elastic by itself, such as plastic tape or string, is not preferable because it makes the force to pull up the panty directly work as a force to pull up the sanitary napkin, and thus makes the sanitary napkin to dig excessively into the gap of the body.

The longitudinal direction of the slightly elastic member and the longitudinal direction of the highly elastic member correspond to the direction to pull up and down the panty when wearing (Y-direction in FIG. 1 and FIG. 2) and to the direction from the crotch part and the leg openings toward the waist part. The crotch portion means the portion of the body between the legs and includes portions such as the ostium vagina, the perineum, and the anal. The elastic coefficient means a value obtained by dividing the tensile load exerted when the members (the slightly elastic member, the highly elastic member, the napkin lifting part, and the fixing member) of the panty are pulled up and extended by a rate of extension at that time, and the larger the elastic coefficient is, the lesser the likelihood of extension becomes.

(3) A panty comprising: a front part, a back part, a crotch part provided so as to bridge between the front part and the back part, the crotch part being utilized for fitting a sanitary napkin, a waist opening part provided in an upper edge of the front part and an upper edge of the back part, and a pair of leg openings provided below both side edges of the front part and both side edges of the back part; wherein a napkin lifting part is provided in a middle of the crotch part from the front part to the back part; and wherein a longitudinal elastic coefficient of the napkin lifting part is larger than a longitudinal elastic coefficient of a cloth constituting the crotch part.

According to the present invention, since the longitudinal elastic coefficient of the napkin lifting part is larger than that of the crotch cloth therearound, the napkin lifting part is pulled up by a force larger than a force pulling up the cloth therearound, which exerts a force to lift the center portion of the sanitary napkin attached to the crotch part (toward the crotch portion of the body). The elasticity of the napkin lifting part ranges from 5 N to 30 N in elastic coefficient, and more preferably, from 10 to 25 N. When the elastic coefficient is smaller than 5 N, a force to suspend the center portion of the sanitary napkin does not work effectively with respect to the pulling up force of the slightly elastic member. As described in (1), since the crotch part is provided so as to bridge between the front part and the back part, it is positioned around the pubic bone and the portion backward of the anal in the worn state. Therefore, when the wearer attaches the sanitary napkin to the crotch part and wears the panty, the sanitary napkin may be stably attached to the crotch part, and thus the sanitary napkin is prevented from kinking, thereby avoiding the risk of leakage of menstrual blood. When providing a waterproof cloth having a waterproof property on inside of the crotch cloth constituting the crotch part, the waterproof cloth may be stitched together with the crotch cloth and the front part or with the crotch cloth and the back part along the stitched portions stitching the crotch cloth and the front part or the back part. Therefore, the number of stitching portions does not increase, and thus the uncomfortable sensation in the worn state or impair of appearance may be prevented. The longitudinal direction of the napkin lifting part is the direction lying between the front part and the back part.

(4) A panty comprising a front part, a back part, a crotch part provided so as to bridge between the front part and the back part, the crotch part being utilized for fitting a sanitary napkin, a waist opening part provided in an upper edge of the front part and an upper edge of the back part, a pair of leg openings provided below both side edges of the front part and both side edges of the back part; and a slightly elastic member made of a slightly elasticated material provided in a highly elastic member made of a highly elasticated material; wherein the slightly elastic member is provided in a substantially center area of the back part from the crotch part to the waist opening part; wherein a napkin lifting part is provided in a middle of the crotch part from the front part to the back part; wherein the slightly elastic member and the napkin lifting part are stitched together at an end of the crotch part on the side of the back part; wherein a longitudinal elastic coefficient of the slightly elastic member is larger than a longitudinal elastic coefficient of the highly elastic member; and wherein a longitudinal elastic coefficient of the napkin lifting part is larger than a longitudinal elastic coefficient of a crotch cloth constituting the crotch part.

According to the present invention, as described above in (2) and (3), the force to pull up the slightly elastic member works as a force to pull up the napkin lifting part when the panty is worn. The napkin lifting part is pulled up with a force larger than the force pulling up the cloth constituting the crotch part therearound, and works as a force to lift the center portion of the sanitary napkin attached to the crotch part upward (toward the crotch portion of the body). Therefore, the sanitary napkin is fixed so as to fit better to the crotch portion. As described in (1), since the crotch part is provided so as to bridge between the front part and the back part, it is positioned around the pubic bone and the portion backward of the anal in the worn state. Therefore, when the wearer attaches the sanitary napkin to the crotch part and wears the panty, the sanitary napkin may be stably attached to the crotch part, and thus the sanitary napkin is prevented from kinking, thereby avoiding the risk of leakage of menstrual blood.

(5) The panty as described in any one of (1) to (4), wherein the crotch part is formed by providing the crotch cloth stitched with the front part and with the back part.

According to the present invention, stitched portions exists between a lower end of the front part and a front end of the crotch cloth and between a lower end of the back part and a rear end of the crotch cloth, respectively, and does not exist at the midsection of the crotch part in a widthwise direction (direction facing toward the pair of leg openings). In other words, the respective stitching portions are positioned around the pubic bone and the portion backward of the anal in the worn state. Therefore, when the wearer attaches the sanitary napkin to the crotch part and wears the panty, the sanitary napkin may be stably attached to the crotch part, and thus the sanitary napkin is prevented from kinking, thereby avoiding the risk of leakage of menstrual blood.

(6) The panty according to any one of (1) to (5), wherein the panty further comprises a waist hold part provided around the waist opening part extending from the back part to the front part.

According to the present invention, the waist hold part disperses a force to pull up the slightly elastic member and a force to fix the fixing member laterally (widthwise) of the panty and holds the forces at the waist portion, the panty is fitted around the waist portion over a wide area.

(7) The panty according to any one of (1) to (6); wherein the panty comprises a fixing member in a substantially center area of the front part stitched on the crotch part, the waist hold part, and the highly elastic member on an external side of the highly elastic member.

According to the present invention, the fixing member may control the highly elastic member to extend when the napkin lifting part is pulled toward the back part by the force carried by the slightly elastic member pulled up when the panty is wearing. Accordingly, since the portion of the napkin lifting part disposed on the side of the front part is fixed without being pulled by the influences of the napkin lifting part and the slightly elastic member, the force for pulling the slightly elastic member works directly as the force to pull up the napkin lifting part, and thus the sanitary napkin is pulled up toward the body and fitted better to the crotch portion and the gluteal cleft.

(8) The panty according to (1), (2) or (4) to (7), wherein the slightly elastic member is formed of a material which is non-elastic in a longitudinal direction.

According to the present invention, since the slightly elastic member has almost no elasticity in the longitudinal direction, when the wearer attaches the sanitary napkin for night use to the napkin fitting cloth and pulls the panty up for wearing it, the pulling up force works effectively as a force to suspend the sanitary napkin. The slightly elastic member that can be employed here is a cloth formed of knitted fabric, such as nylon fiber or polyester fiber, including no elastic member such as polyurethane fiber in the longitudinal direction, and having slight elasticity caused by variations of knitting structure but having no elasticity generated by the property of the member.

(9) The panty according to any one of (3) to (8), wherein the napkin lifting part is formed of a material which is non-elastic in the longitudinal direction.

According to the present invention, since the napkin lifting part has almost no elasticity in the longitudinal direction, when the wearer pulls up the panty for wearing, the napkin lifting part is pulled by the pulling up force transmitted from the slightly elastic member which is stronger than the force exerting to the cloth therearound, and such pulling up force works as a force to lift up the center portion of the sanitary napkin. The napkin lifting part employed here is a cloth formed of knitted fabric, such as nylon fiber or polyester fiber as it is for the slightly elastic member, including no elastic member such as polyurethane fiber in the longitudinal direction, and having slight elasticity caused by variations of knitting structure but having no elasticity generated by the property of the member.

(10) The panty according to any one of (3) to (9), wherein the longitudinal elastic coefficient of the napkin lifting part is smaller than the longitudinal elastic coefficient of the slightly elastic member.

When the panty is worn, the slightly elastic member of the back part works to fit the sanitary napkin to the body while extending the napkin lifting part of the crotch part. In case that the napkin lifting part has larger longitudinal elastic coefficient than the slightly elastic member, when the panty is pulled up, the napkin lifting part does not extend and the slightly elastic member of the back part extends, and thus can hardly exert a force to pull up the sanitary napkin toward the body.

(11) The panty according to any one of (3) to (10), wherein a width of the napkin lifting part is tapered from the front part to the back part.

According to the present invention, the napkin lifting part is pulled toward the back part by a force to pull up the slightly elastic member and exerts a force to suspend the napkin upward (toward the crotch portion of the body) so as to bridge the gap of the body. In this case, since the width of the napkin lifting part is tapered gradually from the portion where the napkin lifting part is connected to the front part (the portion which comes into contact with the portion around the pubic bone), which is the widest portion, toward the portion of ostium vagina, perineum, and anal, an upward force is exerted along the centerline of the sanitary napkin attached to the crotch part with respect to the portion therearound. Then, when the width of the portion where the fixing member is connected to the front part is substantially the same width as the width of the crotch portion, the portion of the panty with which the portion around the pubic bone comes into contact is stabilized, and may be centered on the portion around the ostium vagina. The width on the side of the fixing member being narrow as the portion around the perineum or the anal is not preferable because the center of the sanitary napkin may be shifted in the worn condition, and hence shifted from the center of the ostium vagina.

The width of this napkin lifting part may be tapered gradually from the portion where the fixing member is connected to the front part (the portion that comes into contact with the body portion around the pubic bone), which is the widest portion, toward the portion around the ostium vagina and the perineum, and then increased from the portion around the ostium vagina to the portion around the anal (but narrower than the width of the portion stitched to the fixing member).

(12) The panty according to (11), wherein the width of the napkin lifting part ranges between 20 mm and 60 mm.

According to the present invention, since the width of the napkin lifting part does not assume a narrow line, the force does not concentrate on a single point. Therefore, the possibility of the napkin to dig into the body in the worn state, or of being bent and folded at the center to form an upward projection with the top of the bent giving uncomfortable feeling to the wearer's body when the napkin is attached to the napkin fitting cloth may be reduced.

(13) The panty according to any one of (7) to (12), wherein the longitudinal elastic coefficient of the fixing member is larger than the elastic coefficient of the highly elastic member in the longitudinal direction.

According to the present invention, the fixing member at the center of the front part works as a force to fix the portion of the panty with which the portion around the pubic bone comes into contact. However, since the longitudinal elastic coefficient of the fixing member is larger than the longitudinal elastic coefficient of the highly elastic member, the front part is controlled to extend in the longitudinal direction is controlled. Since the extension is controlled by the fixing member, the center area of the front part does not extend by the influence of the slightly elastic member or the napkin lifting part, and thus the portion of the panty with which the pubic bone comes into contact is fixed. The longitudinal elastic coefficient of the fixing member is in the range from 10 N to 30 N, and more preferably in the range from 15 N to 25 N.

This is because the portion of the front part corresponding to the belly is a portion that is largely deformed by the movement of the body, and thus when it is formed of a cloth that does not extend at all, the waist part at the upper end of the front part slips downward, thereby losing the fitting property. The fixing member is formed of a power net constructed of nylon fiber and polyurethane fiber.

The longitudinal direction of the fixing member here means a direction to pull up and down the panty when wearing, that is, the direction from the crotch part to the leg opening toward the waist part (Y-direction in FIG. 2).

(14) The panty according to any one of (1), (2), or (4) to (13), wherein an upper end of the slightly elastic member on a side of the waist opening part is stitched with the waist hold part in substantially V-shape.

According to the present invention, the length of the cloth constituting the slightly elastic member from the waist hold part to the crotch part is such that the length from the center of the V-shape stitched with the waist hold part (the center point of the V-shape) to the crotch part is shorter than the left and right ends thereof. Since the amount of extension is larger at the shorter portion of the cloth than at the longer portion thereof when the cloth is extended, the portion from the center of the V-shape to the crotch part is pulled up by a force larger than the force exerted to the left and right ends thereof when the slightly elastic member is pulled upward. Therefore, the center portion does not slack and thus a force to pull up the sanitary napkin is generated.

(15) The panty according to (6) to (13), wherein an upper end of the fixing member on a side of the waist opening part is stitched with the waist hold part in substantially V-shape.

According to the present invention, the length of the cloth constituting the fixing member extending from the waist hold part to the crotch part is such that the length of the center of the fixing member (the pointed top of the V-shape) is shorter than the left and right ends thereof. Since the amount of extension when extended is larger at the shorter portion of the cloth than at the longer portion thereof, the center portion from of the fixing member is pulled up by a force larger than the force exerted to the left and right ends thereof when the fixing member is pulled upward. Therefore, the center portion does not slack and thus a force to pull up the sanitary napkin is generated.

(16) The panty according to any one of (1) to (15), wherein the crotch part comprises a napkin fitting cloth inside, front and rear ends of the napkin fitting cloth being stitched with the crotch part and side ends of the napkin fitting cloth being unstitched on the crotch part.

According to the present invention, the sanitary napkin fitting cloth is stitched to the crotch part only at the front and rear ends and is not completely integrated with the crotch part, that is, it is independent from the crotch part on the inside of the crotch part. Therefore, since the napkin fitting cloth does not extend in the fore-and-aft direction (in the direction toward the front part and the back part) together with the crotch part, or even when it extends, the amount of extension is very little, the sanitary napkin attached thereto may be reliably held. In addition, since it is stitched with the crotch part at the front and rear ends, it may be stitched together with the crotch cloth which constitutes the crotch part. Therefore, the number of stitching portions does not increase, and thus uncomfortable feeling in the worn state or impair of appearance may be prevented. The front and rear ends mean the ends of the napkin fitting cloth on the side of the front part and on the side of the back part.

(17) The panty according to (16), wherein a length of the napkin fitting cloth is equivalent to or longer than a length of the crotch cloth constituting the crotch part.

According to the present invention, since the length of the napkin fitting cloth is long enough not to extend, even when the crotch part formed of the crotch cloth of elastic fabric is extended when the wearer pulls up the panty for wearing, or even when it extends, the amount of extension is very little, and thus the sanitary napkin can be reliably held. When the crotch part is extended, the napkin lifting part is pushed toward the crotch portion and thus the sanitary napkin is pushed toward the crotch portion.

(18) The panty according to (1), (2), or (4) to (17), wherein an elasticity gradually decreases from the highly elastic member to the slightly elastic member at a boundary between the highly elastic member and the slightly elastic member.

According to the present invention, since the elasticity gradually decreases from the highly elastic member, when the wearer pulls up the panty for wearing, the extension of the slightly elastic member gradually decreases and thus the panty can fit the wearer's body without giving uncomfortable feeling.

(19) The panty according to any one of (1), (2) or (4) to (17), wherein an elasticity changes discontinuously from the highly elastic member to the slightly elastic member at a boundary between the highly elastic member and the slightly elastic member.

By providing elasticity of the slightly elastic member so as to change discontinuously from the highly elastic member to the slightly elastic member, the highly elastic member and the slightly elastic member are apparently divided. In comparison with the case in which they are not apparently divided (that is, the case in which the elasticity continuously changes), the fitting property may be lowered, but the effect of lifting the sanitary napkin is enhanced.

(20) The panty according to any one of (1) to (19), wherein when the panty assumes a three-dimensional configuration, a dimensional ratio between a center height length from the crotch part to the waist opening part and the side height length which is a shortest length ranging from the leg openings to the waist opening part is set at 100 for the former and at between 80 and 200 for the latter.

According to the present invention, since the side height length of the panty is long, the leg bands provided at the leg openings do not tighten from the portion around the crotch portion to the side bone, but tighten the femoral regions of the wearer. Therefore, since the oblique pulling-up force generated by the leg bands does not act on the crotch part, digging into the crotch portion does not occur. In addition, since a large pulling-up force generated by the leg bands does not act on the crotch part, the sanitary napkin on the crotch part is reliably suspended upward by the slightly elastic member provided on the back part, thereby achieving better fit.

(21) The panty according to any one of (1) to (20), wherein the slightly elastic member, the napkin lifting part, and the waist hold part exhibit different color tones or glosses from the highly elastic member.

According to the present invention, since the slightly elastic member, the napkin lifting part, and the waist hold part are different in color or texture from the highly elastic member, they can be visually distinguished. In this manner, since the waist hold part, the slightly elastic member, and the napkin lifting part are outstanding, the wearer can easily recognize these lifting members, and can realize the effect of the lifting members easily. Since these lifting members provided at the center of the panty have different appearance from other cloth members, when the wearer attaches and positions the sanitary napkin to the panty, the center of the sanitary napkin and the center of the panty can easily be aligned, and thus the center of the sanitary napkin can be fitted to the center of the crotch portion of the body adequately. Accordingly, the effect to block the gap for preventing leakage of liquid such as menstrual blood can be improved.

(22) The panty according to any one of (1) to (21), comprising an instruction showing how to wear on the front part or on the back part.

According to the present invention, the wearer can control the fitting property of the sanitary napkin by viewing the instruction. The wearer attaches the sanitary napkin to the napkin fitting cloth on the panty via an adhesive agent or the like, and pulls up the panty by holding the upper side portion thereof when pulling up and wearing the panty to the prescribed position of the body. This way of wearing may also provide some degrees of adhesion to the sanitary napkin. However, since desired degree of adhesion differs on an individual basis, those who want to achieve better fit can obtain adhesion of their preference by following the instruction, for example, saying that "better fitting may be achieved by pulling the portion located on the extension of the slightly elastic member at the center of the back part". In this manner, those who want to have high adhesion are guided so that they can recognize how to wear with ease.

(23) The panty according to (22), wherein the instruction is provided near the waist opening part above the slightly elastic member.

According to the present invention, the sanitary napkin can be fitted better by pulling up the portion of the instruction. In other words, the slightly elastic member is pulled up by pulling the portion of the instruction further upward after wearing the panty by holding the upper side portions of the panty. By the slightly elastic member being pulled up, the sanitary napkin can be pushed toward the crotch portion of the body more firmly as described above, and thus higher adhesion may be obtained.

DESCRIPTION OF THE PREFERRED EMBODIMENT

Figure 1:
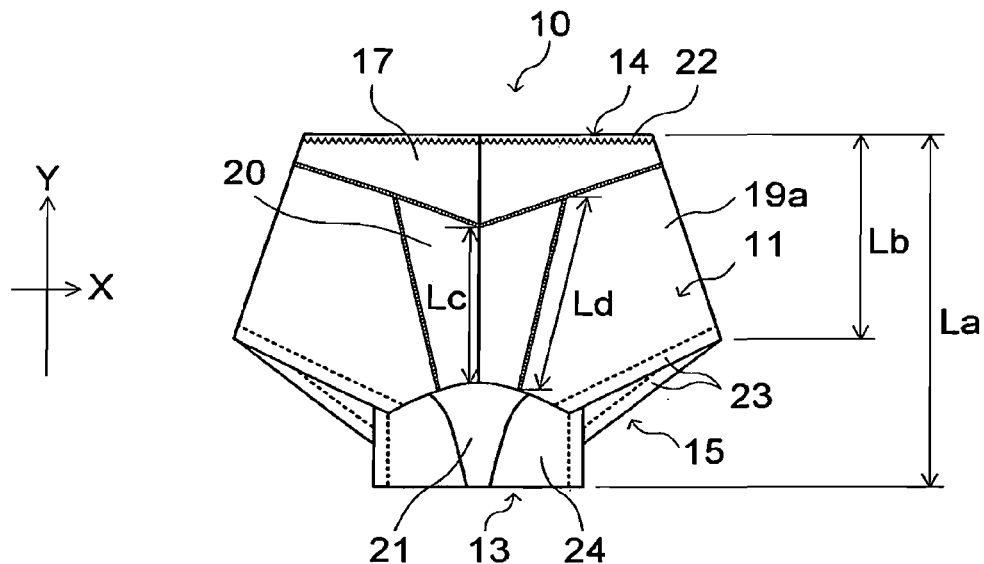
FIG. 1 is a front view showing a first embodiment of a panty according to the present invention, which is shown in a state in which the panty is folded into two so that the front part and the back part come in contact with each other.

Referring now to the drawings, an embodiment of a panty according to the present invention will be described. It should be understood that the present invention is not limited thereto.

Figure 2:
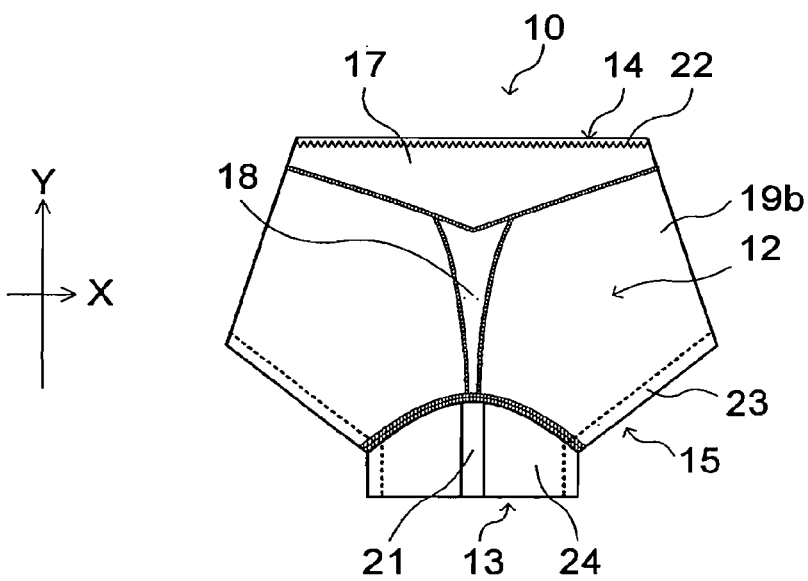
FIG. 2 is a back view showing the panty according to the embodiment in a state of being folded into two.
Figure 3:
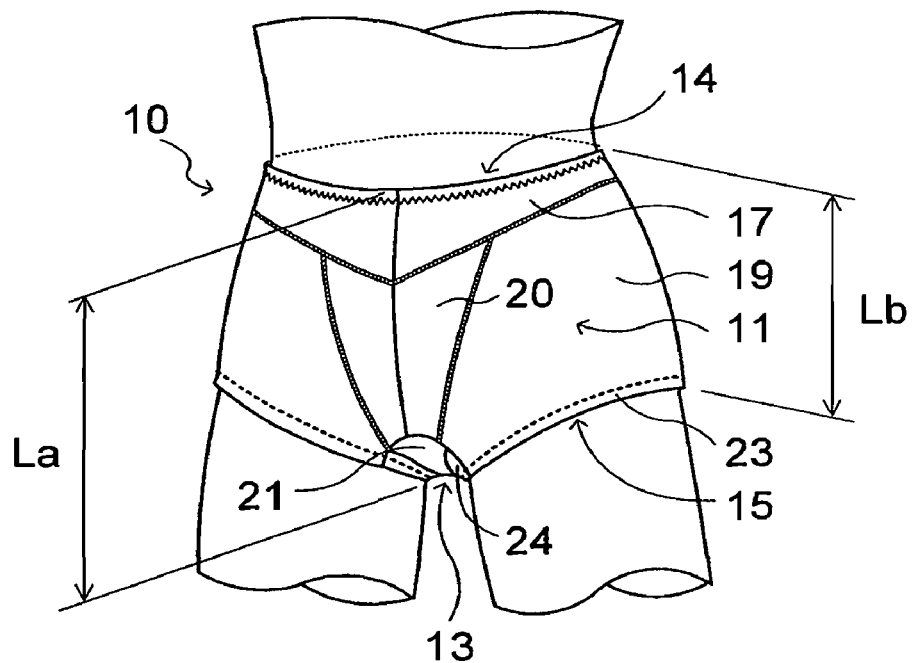
FIG. 3 is a perspective view showing the panty according to the embodiment, which is shown in a state in which it is worn as viewed from the side of the front part.
Figure 4:
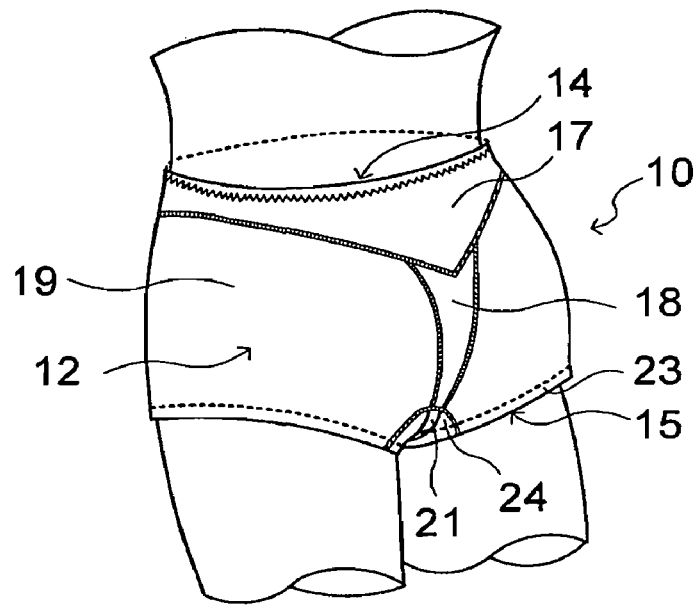
FIG. 4 is a perspective view showing the panty according to the embodiment, which is shown in a state in which it is worn as viewed from the side of the back part.
Figure 5:
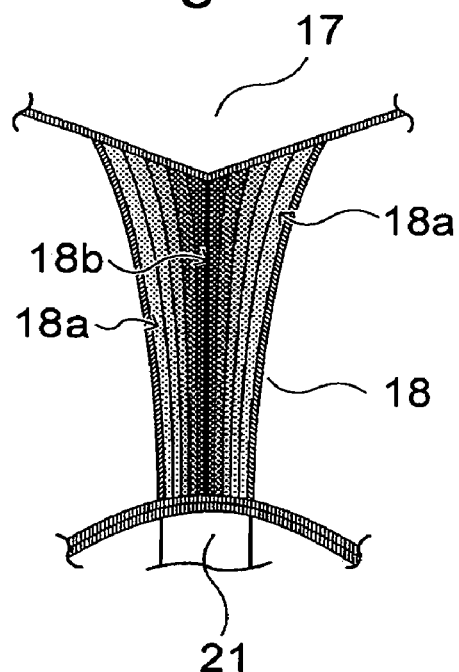
FIG. 5 is an enlarged plan view of a slightly elastic member of the panty according to the embodiment.
Figure 6:
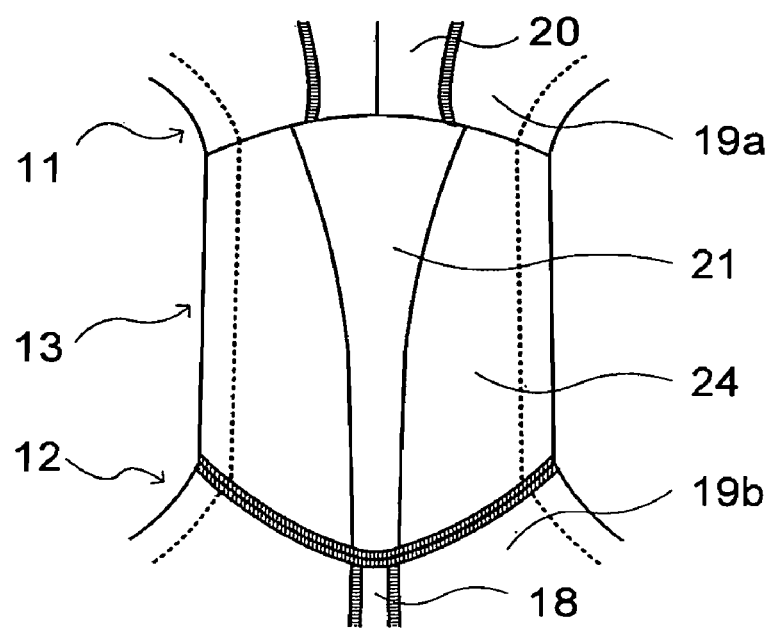
FIG. 6 is a partial plan view of a crotch part of the panty according to the embodiment as viewed from the bottom side.
Figure 7:
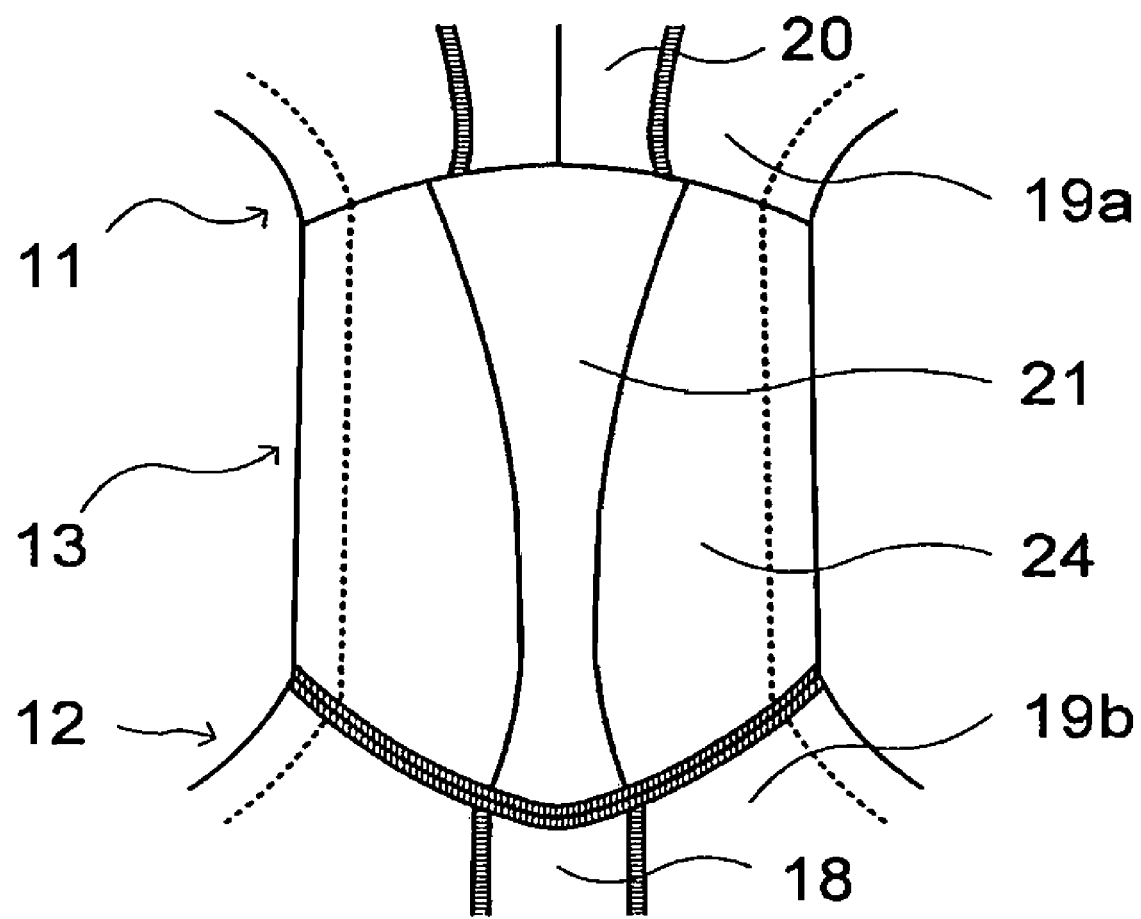
FIG. 7 is a partial plan view of a crotch part which has a different napkin lifting part the napkin lifting part of the embodiment.
Figure 8:
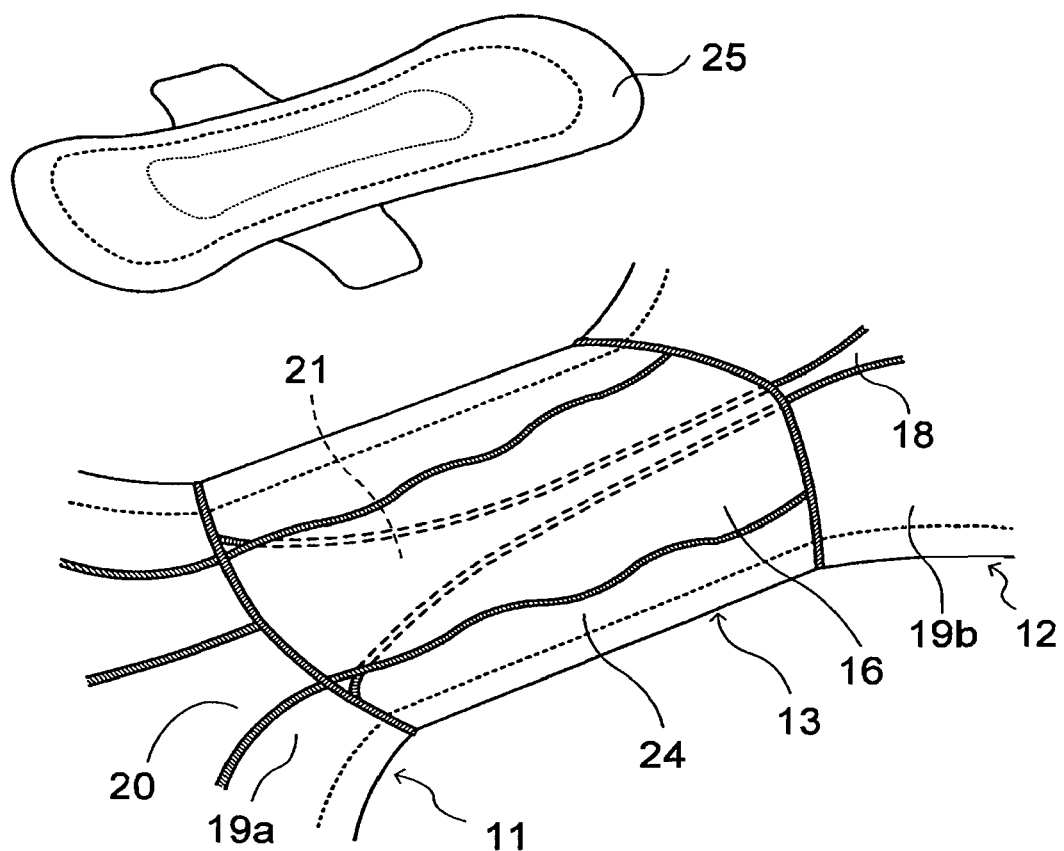
FIG. 8 is a partial perspective view of the crotch part of the panty according to the first embodiment as viewed from inside.
Figure 9:
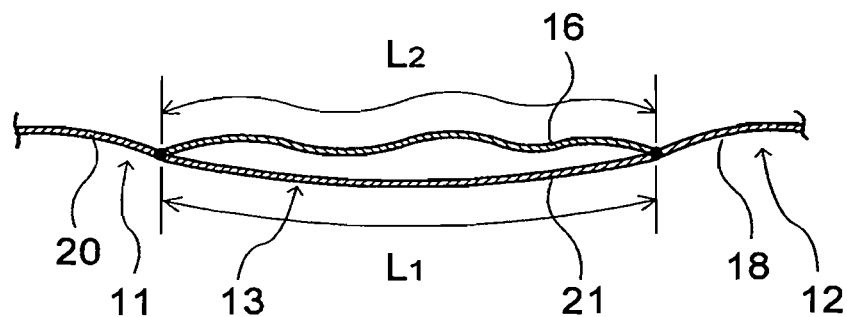
FIG. 9 is a partial side view of the crotch part according to the embodiment.
Figure 10:
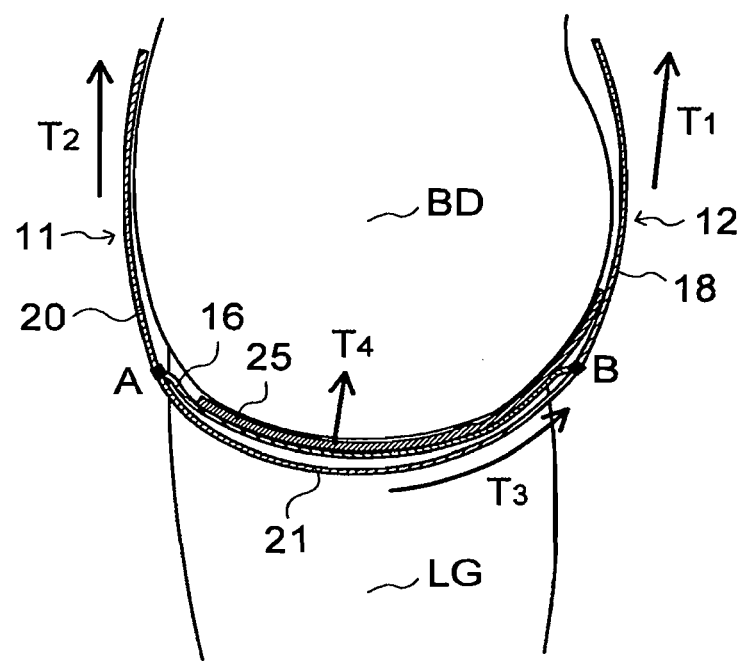
FIG. 10 is an explanatory drawing showing how a slightly elastic member, a napkin lifting part, and a fixing member move when the panty is worn.
Figure 11:
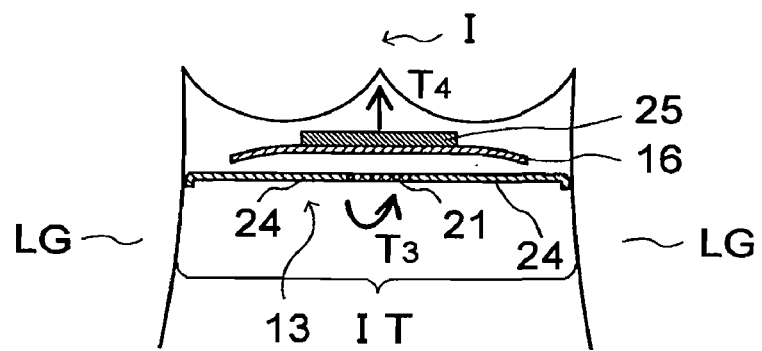
FIG. 11 is an explanatory drawing showing how the portion of the panty positioned in the vicinity of the ostium vagina move when the panty is worn.
Figure 12:
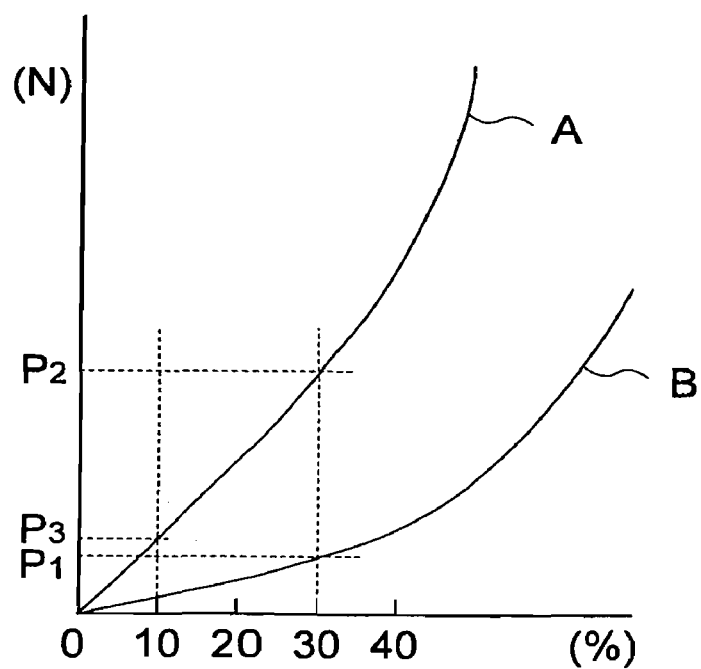
FIG. 12 is a drawing showing the relation between the rate of extension and the tensile strength of the slightly elastic member.

FIG. 1 is a front view of a panty according to a first embodiment of the present invention, which is shown in a state in which the panty is not worn on the body and is folded into two so that the front part and the back part come into contact with each other. FIG. 2 is a back view showing the panty shown in FIG. 1, which is folded into two; FIG. 3 is a perspective view of the panty of the first embodiment showing a state in which the panty is worn and viewed from the side of the front part; FIG. 4 is a perspective view of the panty of the first embodiment showing a state in which the panty is worn and viewed from the side of the back part; FIG. 5 is an enlarged plan view showing the slightly elastic member of the panty according to a second embodiment in the enlarged state; FIG. 6 is a partial plan view of the crotch part when viewed from the bottom side; FIG. 7 is a partial plan view showing a different napkin lifting part from what is shown in FIG. 6; FIG. 8 is a partial perspective view showing the crotch part viewed from the inside; FIG. 9 is a partial side view of the crotch part; FIG. 10 is an explanatory drawing showing how the slightly elastic member, the napkin lifting part, and the fixing member of the panty move when the panty is worn; FIG. 11 is an explanatory drawing showing how the portion of the panty positioned around the vicinity of ostium vagina move when the panty is worn, and FIG. 12 is a drawing showing the relation between the rate of extension and the tensile strength of the slightly elastic member.

As shown in FIG. 1 to FIG. 4, the panty 10 has a front part 11, a back part 12, a crotch part 13 positioned between the front part 11 and the back part 12. A waist opening part 14 is formed in an upper edge of the front part 11 and an upper edge of the back part 12, a pair of leg openings 15 are formed below the front part 11 and the back part 12, and a napkin fitting cloth 16 (shown in FIG. 8) on which a sanitary napkin is attached is disposed inside of the crotch part 13. A waist hold part 17 extending from the front part 11 to the back part 12 is provided around a waist opening part 14, and a slightly elastic member 18 extending from the crotch part 13 to the waist hold part 17 is disposed at a center area of the back part 12. A highly elastic member 19 is disposed in all the other area of the front part 11 and the back part 12 except for the waist hold part 17 and a fixing member 20 and it is stitched at a substantially center of the front part 11. A part of the highly elastic member 19 which is disposed in the back part 12 forms a back side highly elastic member 19b which extends from the slightly elastic member 18 to the front part 11. The other part of the highly elastic member 19 which is disposed in the front part 11 forms a front side highly elastic member 19a. In the center area of the front part 11, the fixing member 20 is provided, and the fixing member 20 is stitched with the highly elastic member 19. The highly elastic member 19 is stitched also with the crotch part 13 and the waist hold part 17 both in the front part 11 and the back part 12. And a napkin lifting part 21 is provided in a middle of the crotch part 13 bridging the slightly elastic member 18 with the fixing member 20. A waist band 22 is provided along the upper side of the waist hold part 17 which is formed in the upper edges of the front part 11 and the back part 12, and leg bands 23 are provided around the leg openings 15. A dimensional ratio between a center height length La ranging from the crotch part 13 to the waist opening part 14 and a side height length Lb which is the shortest length ranging from the leg openings 15 to the waist opening part 14 is between 80 and 200 as taking that the center height length is 100.

The highly elastic member 19 may be formed of a knitted fabric, such as a combination of a nylon fiber and a polyurethane fiber, a combination of a polyester fiber and a polyurethane fiber, or a combination of a nylon fiber, a polyester fiber and a polyurethane fiber. Other knitted fabric than the above-described combinations may be used as long as the elastic coefficient does not exceed 10 N. The crotch part 13 is formed by providing a crotch cloth 24, and the crotch cloth 24 is stitched with the highly elastic member 19 on a side of the front part 11 and a side of the back part 12. The crotch cloth 24, similar to the highly elastic member 19, is formed of a resiliently stretchable knitted fabric such as the combination of the nylon fiber and the polyurethane fiber, the combination of the polyester fiber and the polyurethane fiber, or the combination of the nylon fiber, the polyester fiber and the polyurethane fiber. The waist band 22 provided along the waist opening part 14 and the leg bands 23 provided along the leg openings 15 are formed of elastic material such as elastic woven fabric of polyurethane fiber, synthetic rubber sheet, or natural rubber sheet. The longitudinal direction here means a direction when the waist opening part 14 and the crotch part 13 are defined to be upper and lower sides (Y-direction in FIG. 1), that is, a direction to pull up and down the panty 10 when it is wearing, and the lateral direction means a direction orthogonal to the longitudinal direction (X-direction in FIG. 1), that is, a widthwise direction of the panty 10.

The waist hold part 17 is formed around the waist opening part 14 of the panty 10 to form V shaped edge, the pointed edge of which points to the centers of the front part 11 and the back part 12, and is stitched with the highly elastic member 19 of the front part 11 and the back part 12. The waist hold part 17 is a knitted fabric whose elastic coefficient in the longitudinal direction is higher than the elastic coefficient in the lateral direction. The knitted fabric is the combination of the nylon fiber and the polyurethane fiber, the combination of the polyester fiber and the polyurethane fiber, or the combination of the nylon fiber, the polyester fiber and the polyurethane fiber for example. The waist band 22 provided around the waist opening part 14 is, for example, a polyurethane band, a natural rubber band, or a synthetic rubber band of about 10 mm and is stitched with the waist hold part 17 in an extended state.

The waist hold part 17 functions to disperse a force to pull up the napkin lifting part 21 through the slightly elastic member 18 or the fixing member 20 and to hold the force at the waist portion, and thus it is desirable that the longitudinal extension of the waist hold part 17 is restricted so that the waist hold part 17 is held and fixed at the waist portion when the panty 10 is worn. It is desirable that a lateral elastic coefficient thereof is larger than a lateral elastic coefficient of the highly elastic member 19, because a force constricting the waist opening part 14 increases and hence the panty 10 is prevented from slipping down.

The slightly elastic member 18 is provided in the substantially center area of the back part 12. The upper end of the slightly elastic member 18 is stitched with a center portion of the waist hold part 17 (the portion in the vicinity of the pointed edge of the V-shaped edge), and the lower end of the slightly elastic member 18 is stitched with an end of the crotch part 13 on the side of the back part 12 (a rear end of the crotch part 13) and both side ends of the slightly elastic member 18 are stitched with the highly elastic member 19. The slightly elastic member 18 extends from the waist hold part 17 to the rear end of the crotch part 13, and is tapered toward the rear end of the crotch part 13. The width of the narrow portion ranges from 10 mm to 30 mm, and preferably, is about 20 mm. The width of the wide portion where the slightly elastic member 18 is stitched with the waist hold part 17 is in the range from 30 mm to 130 mm, and preferably about 60 mm. The slightly elastic member 18 may be extended to the waist opening part 14.

The length of a middle area of the slightly elastic member 18 (corresponds to Lc in FIG. 1) is shorter than lengths of the side ends of the slightly elastic member 18 (corresponds to Ld in FIG. 1), and the upper end of the slightly elastic member 18 and the rear end of the waist hold part 17 are stitched with each other to form a V-shaped portion having the V-shaped edge as described above. Therefore, a cloth positioned in the middle area of the slightly elastic member 18 extending from the pointed edge of the V-shaped portion to the crotch part 13 is extended more than clothes positioned in the side ends of the slightly elastic member 18 when the panty 10 is worn. That is, an extension force lifting the cloth positioned in the middle area of the slightly elastic member 18 is larger than the one lifting the clothes positioned in side ends of the slightly elastic member 18. When the slightly elastic member 18 is pulled upward, since the length of the middle area of the slightly elastic member 18 is shorter than those of the side ends of the slightly elastic member 18, the cloth positioned in the middle area is pulled up by a larger force than the force pulling up the clothes positioned in left and right ends thereof. Therefore, the center portion does not go slack and thus a force to pull up the sanitary napkin 25 is generated. Regarding the relation between these lengths, dimensions and elastic rates were measured before and after the panty 10 is put on a doll. The dimensions and elastic rates are shown in Table 1. As shown in Table 1, the length at the middle area of the slightly elastic member 18 is shorter before the panty 10 is worn, and the elastic rate when it is worn is large.

TABLE 1

The lengths and the elastic rates of clothes used for the slightly elastic member and the fixing member.

| | Slightly elastic member | | Fixing member | |
|---|---|---|---|---|
| | Center portion (Middle area) (Lc) | Side portion (Right and left ends) (Ld) | Center portion (Lc) | Side portion (Ld) |
| Length before worn (cm) | 13.0 | 14.5 | 7.5 | 12.0 |
| Length in worn state (cm) | 16.0 | 17.0 | 10.4 | 15.0 |
| Elastic rate (%) | 23.1 | 17.2 | 38.7 | 25.0 |

1) Center portion (Lc): the length extending from the pointed edge of the V-shaped portion to the crotch part.
2) Side portion (Ld): the length of the side line extending from the side of the V-shaped portion to the crotch part.

The slightly elastic member 18 may be formed of a knitted fabric such as the combination of the nylon fiber and/or the polyester fiber, the combination of the nylon fiber and the polyurethane fiber, the combination of the polyester fiber and the polyurethane fiber, or the combination of the nylon fiber, the polyester fiber, and the polyurethane fiber. The cloth forming the slightly elastic member 18 has no elastic material such as polyurethane fiber in the longitudinal direction so that it has slight elasticity caused by knitting structure but has no elasticity generated by the material itself, that is, the cloth having a larger longitudinal elastic coefficient than the longitudinal elastic coefficient of the highly elastic member 19. Therefore, the slightly elastic member 18 can hardly be extended in comparison with the highly elastic member 19. In this structure, since the highly elastic member 19 covering the hip and the belly of the body therearound is formed of the cloth which is elastic longitudinally and laterally, it follows the deformation of the body caused by the movement of the wearer. However, the slightly elastic member 18 provided substantially in the center area of the back part 12 is hardly affected by the movement of the highly elastic member 19 because the longitudinal elastic coefficient thereof is larger than the elastic coefficient of the highly elastic member 19.

The elasticity of the slightly elastic member 18 is such that the elastic coefficient is preferably in the range from 10 N to 60 N and, more preferably, from 20 N to 50 N. The force to lift the sanitary napkin 25 is not sufficient when the elastic coefficient is smaller than 10 N, and when the elastic coefficient is larger than 60 N, the sanitary napkin 25 may dig into the gap of the body too strong. (FIG. 11) Although the force to pull up the panty 10 directly works as a force to pull up the sanitary napkin 25 even when the slightly elastic member 18 does not extend at all, a force to pull up the sanitary napkin 25 is larger than the force required for fitting the sanitary napkin 25 which may make the is sanitary napkin 25 dig the body excessively and cause uncomfortable feeling or pain, which is not desirable. In contrast, when the elasticity is too large, the slightly elastic member 18 extends excessively when the wearer pulls up the panty 10, and thus does not work effectively as a force to pull up the sanitary napkin 25.

On the other hand, the elastic coefficient of the highly elastic member 19 is less than 10 N, and more preferably, in the range from 2 N to 3 N when extended between 10 and 30%. More specifically, the tensile load exerted when the panty is extended about 20% in the worn state is in the range from 0.4 to 0.6 N, so that comfortable gentle fitting along the body is achieved. The elastic coefficient in the worn state means the elastic coefficient obtained when the panty is put on the doll assuming medium size.

The slightly elastic member 18 may be formed such that the extension rate is the same throughout the area, or may be formed such that the extension rate changes gradually or discontinuously to decrease from the left and right ends toward the middle area as shown in FIG. 5. FIG. 5 shows the slightly elastic member 18 in an enlarged manner, in which the slightly elastic member 18 is shown in a state in which the extension rate changes gradually from the left and right ends 18a toward the middle area 18b in a schematic manner.

Just for reference, the relation between the extension rate and the tensile strength of the slightly elastic member 18 of the panty 10 according to the present invention is shown in FIG. 12 in comparison with the panty in the related art. In FIG. 12, the vertical axis represents the tensile load with the unit of Newton (N), and the lateral axis represents the extension rate with the unit %. A curve A corresponds to the panty according to the present invention and the curve B corresponds to the panty in the related art.

As shown in FIG. 12, when the slightly elastic member provided in the substantially center area of the back part of the panty in the related art extends 30%, the tensile load applied is P1. On the other hand, when the slightly elastic member 18 of the panty 10 according to the present invention extends 30%, the tensile load applied is P2, which means that the panty 10 of the present invention is larger tensile strength than the panty in the related art. In other words, the panty 10 of the present invention has larger tensile load than that of the panty in the related art with the same extension rate. Even when the panty 10 according to the present invention extends only 10% in the worn state, the tensile strength applied to the panty 10 of the present invention is P3 which is larger than the tensile strength of the panty in the related art. In other words, even when the extension rate is smaller than the panty in the related art, the tensile strength applied to the panty 10 of the present invention is larger, which means that the slightly elastic member 18 of the panty 10 of the present invention works effectively as the force to pull the crotch part 13. Therefore, the force to pull up the sanitary napkin 25 for night use increases, so that the sanitary napkin 25 fits better to the crotch portion of the body.

The fixing member 20, of the panty 10 is formed of a power net, and is disposed in the substantially center area of the front part 11. The upper end thereof is stitched with the waist hold part 17 around the pointed edge of the V-shaped portion of the waist hold part 17, and the side edges thereof are stitched on the highly elastic member 19. The lower end thereof is stitched with the napkin lifting part 21 and the napkin fitting cloth 16 constituting the crotch part 13 or with the highly elastic member 19 at the end of the crotch part 13 on the side of the front part 11 (front end of the crotch part 13). The fixing member 20 is tapered from the waist hold part 17 toward the crotch part 13, and is stitched with the napkin lifting part 21 disposed in the substantially middle of the crotch part 13. The width of the portion where the fixing member 20 is stitched with the napkin lifting part 21 is almost the same as the width of the front end of the napkin lifting part 21 disposed in the side of the front part 11. The upper end stitched with the waist hold part 17 is formed into a substantially V-shape, and the width thereof is in the range from 60 mm to 150 mm, and preferably, in the range from 80 mm to 120 mm.

The length of the center portion of the fixing member 20 (corresponds to Lc in FIG. 1) is shorter than those of the left and right side ends thereof (corresponds to Ld in FIG. 1) and the upper end of the fixing member 20 and the rear end of the waist hold part 17 are stitched to form a V-shaped portion as described above. Therefore, as in the case of the slightly elastic member 18, when the fixing member 20 is pulled upward, the center portion of the fixing member 20 is pulled up by the stronger force than the force lifting the left and right side ends thereof (See Table 1). Therefore, the center portion does not go slack and the force to pull up the sanitary napkin 25 is generated.

The power net constituting the fixing member 20 is a cloth formed of nylon fabric and polyurethane fiber higher than 100 dtex, and the longitudinal elastic coefficient is larger than the longitudinal elastic coefficient of the highly elastic member 19, that is, the power net cloth constituting the fixing member 20 is less elastic than the highly elastic member 19. The longitudinal tensile strength of the fixing member 20 is such that the elastic coefficient is in the range from 10 N to 30 N, more preferably, in the range from 15 N to 30 N. The type or the mixing rate of the fiber in the power net constituting the fixing member 20 is not limited thereto, and may be selected as appropriate so that the above-described effect can be obtained.

As shown in FIG. 6, the napkin lifting part 21 is disposed in the substantially middle of the crotch part 13 formed by providing the crotch cloth 24 which is a similar material as of the highly elastic member 19 and forms a part of the crotch part. One end of the napkin lifting part 21 is stitched with the lower end of the slightly elastic member 18 provided at the substantially center area of the back part 12, and the other end of the napkin lifting part 21 is stitched with the lower end of the fixing member 20 provided at the substantially center area of the front part 11. The both side ends of the fixing member 20 are stitched with the crotch cloth 24 forming the crotch part 13. The napkin lifting part 21 extends from around the portion that comes into contact with the pubic bone to the portion around the anal and tapers from the front end on the side of the front part 11 to the rear end on the side of the back part 12. The width of the napkin lifting part 21 is in the range from 50 mm to 80 mm at the wider portion, and more preferably, about 70 mm, and in the range from 10 to 30 mm at the narrower portion, and more preferably, about 20 mm.

The napkin lifting part 21, similar to the slightly elastic member 18, is formed of a knitted fabric such as the combination of the nylon fiber and/or the polyester fiber, the combination of the nylon fiber and the polyurethane fiber, the combination of the polyester fiber and the polyurethane fiber, or the combination of the nylon fiber, the polyester fiber, and the polyurethane fiber, and includes no elastic material such as polyurethane fiber in the longitudinal direction, and has slight elasticity caused by variations of knitting structure but has no elasticity generated by the material itself. It is formed of a cloth having a longitudinal elastic coefficient smaller than the longitudinal elastic coefficient of the slightly elastic member 18, that is, the cloth constituting the napkin lifting part 21 is more elastic than the slightly elastic member 18.

The elasticity of the napkin lifting part 21 is preferably such that the elastic coefficient is in the range from 5 N to 30 N, and more preferably, in the range from 10 N to 25 N. The force to lift the center portion of the sanitary napkin 25 is not sufficient when the elastic coefficient is smaller than 5 N. When the elastic coefficient is larger than 30 N, the elasticity thereof exceeds that of the slightly elastic member 18, and thus suspending action which makes the center portion of the sanitary napkin 25 fit to the gap of the body can hardly be performed.

The napkin lifting part 21 may be formed in such a manner that the width thereof is tapered gradually from the portion stitched with the fixing member 20, which is the widest portion, toward the intermediate area, and increases again from the intermediate area toward the portion stitched to the slightly elastic member 18, as shown in FIG. 7. In this case, the width of the napkin lifting part 21 at the portion stitched with the slightly elastic member 18 is smaller than the width of the portion stitched with the fixing member 20.

As shown in FIG. 8., the napkin fitting cloth 16 is disposed over the inside of the crotch part 13. The front end of the napkin fitting cloth 16 is stitched on the crotch part 13 on the side of the front part 11 and the rear end of the napkin fitting cloth 16 is stitched on the crotch part 13 on the side of the back part 12. The napkin fitting cloth 16 is a cloth-film integration formed by stitching a waterproof cloth formed of polyurethane-laminated polyester circular dappled knit and polyester knitted fabric for protecting the laminated film surface together around the left and right ends. The length L2 of the napkin fitting cloth 16 is, as shown in FIG. 9, the same as the length L1 of the crotch part 13 or more. More specifically, the length L1 of the crotch part 13 is in a range of 140 mm to 190 mm, and preferably, about 160 mm. The length L2 of the napkin fitting cloth 16 is in a range of 140 mm to 220 mm, and preferably, about 200 mm.

The highly elastic member 19 of the panty 10 is formed of black semi-dull cloth. The waist hold part 17, the slightly elastic member 18, and the napkin lifting part 21 are formed of bright brown cloth. The power net constituting the fixing member 20 may be of different color from the cloth of the highly elastic member 19. In this manner, it is preferable that the waist hold part 17, the slightly elastic member 18, the napkin lifting part 21, and the fixing member 20 are differentiated from the highly elastic member 19 in color or in light reflection by changing the amount of blended titanium oxide whether or not the colors be the same, so that these members for lifting the sanitary napkin are visually distinguishable.

Referring now to FIG. 10 and FIG. 11, the behaviors of the slightly elastic member 18, the napkin lifting part 21, and the fixing member 20 when the panty 10 according to the present invention is worn will be described. FIG. 10 is an explanatory cross-sectional view of the panty around the crotch portion of the body showing how the slightly elastic member, the napkin lifting part, and the fixing member move around the crotch portion of the body when the panty of the present invention is worn. Reference sign BD designates the body, and reference sign LG designates a leg. FIG. 11 is an explanatory lateral cross-sectional view of the portion of the panty around the ostium vagina showing the behavior of the portion of the panty in the vicinity of the ostium vagina in the worn state. Reference sign I in FIG. 11 designates the ostium vagina, and reference numeral IT between both legs LG designates the inside of the femurs.

When the panty 10 is worn, as shown in FIG. 10, a force T3 for pulling the napkin lifting part 21 toward the back part to cover the gap of the body at a point A (a portion where the fixing member and the crotch part 13 are stitched each other, which comes into contact with the pubic bone of the body) as a supporting point is emerged by receiving a lifting force T1 caused the slightly elastic member 18. Then, the force T3 for pulling up the napkin lifting part 21 is exerted as force to pull up the center portion of the sanitary napkin 25 upward. The width of the napkin lifting part 21 around the point A is about 70 mm, and is tapered gradually toward the ostium vagina, the perineum, and the anal (toward a point B, which is a stitched portion between the slightly elastic member 18 and the crotch part 13) into the width of about 20 mm. In this manner, since the width of the napkin lifting part 21 on the point A is wide, the point A is fixed so that the napkin lifting part 21 may be prevented from moving to right or left side and the center of the napkin lifting part 21 may be around the ostium vagina. If the width of the napkin lifting part on the point A is such narrow as 20 mm, the napkin lifting part 21 may be shifted to right or left and hence the center thereof may not be positioned around ostium vagina in the worn state, which is not preferable.

As shown in FIG. 11, since the width of the napkin lifting part 21 in the vicinity of the ostium vagina is as narrow as 20 mm, and the elastic coefficient of the napkin lifting part 21 is higher than the cloth therearound, it is extended by a stronger force and exerts as a force T4 for lifting the center portion of the sanitary napkin 25 upward.

As shown in FIG. 10, the napkin lifting part 21 is pulled toward rearward (the back part 12) by the force T1 caused by the slightly elastic member 18 being pulled toward the upper side of the back part 12. Therefore, a force to shift the napkin lifting part 21 toward rearward is generated at the point A. When the napkin lifting part 21 is shifted rearward along with the point A, the force to make the sanitary napkin 25 fit to the body, which is exerted by the napkin lifting part 21, can hardly be effected. In other words, when the whole of the napkin lifting part 21 is shifted rearward, the force to make the sanitary napkin 25 fit to the body is not generated. In order to avoid such a state, it is preferable to fix the point A as firm as possible. On the other hand, the fixing member 20 of the front part 11 exerts the force to fix the point A. In other words, by stitching the power net which constitutes the fixing member 20 to the outside of the highly elastic member 19 of the panty 10, the force T2 generated in the front part 11 tending to extend in the vertical direction may be lessened. In this manner, the extension of the front part 11 is lessened by stitching the fixing member 20 thereon, and thus the point A is fixed without being pulled by the slightly elastic member 18 and the napkin lifting part 21. The longitudinal elastic coefficient of the cloth of the power net which constitutes the fixing member 20 is preferably in a range of 10 N to 30 N, because if it is formed of non-elastic cloth, the waist opening part at the upper end of the front part 11 may slip downward since the belly with which the front part 11 comes into contact is a significantly deformable portion according to the movement of the wearer, and thus there is a risk of impairing the fitting property.

The point A here corresponds to the stitched portion between the fixing member 20 and the crotch part 13, that is, around the portion which comes into contact with the pubic bone of the body, while the point B corresponds to the stitched portion between the slightly elastic member 18 and the crotch part 13, that is, the portion on the side of the back part 12 with respect to the anal, and the portion about 150 to 200 mm rearward (on the side of the back part 12) from the pubic bone.

A method of measuring the elasticity of the members of the panty (the slightly elastic member, the napkin lifting part, the fixing member, and the highly elastic member) will now be described.

<Measurement of the Slightly Elastic Member>

The stitched portion stitching the rear end of the crotch part 13 with the slightly elastic member 18 on the side of the back part 12 (the rear end of the crotch part 13) and the position at the chucking distance of 100 mm from this stitched portion toward the waist opening part 14 are clamped by a chuck (the dimensions of the clamping surface is rectangular of 30 mm×25 mm), the slightly elastic member 18 is extended by 50% at a pulling speed of 100 mm/min. by a tensile tester, and the tensile loads are measured at every 10% of extension.

<Measurement of the Napkin Lifting Part>

The stitched portion stitching the napkin lifting part 21 with the front part 11 and the position at the chucking distance of 150 mm from the stitched portion toward the back part 12 of the panty 10 are clamped by the chuck (the dimensions of the chucking surface is a rectangular of 35 mm×25 mm), the napkin lifting part is extended by 50% at a pulling speed of 100 mm/min. by the tensile tester, and the tension loads are measured at every 10% of extension.

<Measurement of the Fixing Member>

The stitched portion stitching the fixing member 20 with the end of the crotch part 13 on the side of the front part 11 (the front end of the crotch part 13) and the position at the chucking distance of 80 mm from this stitched portion toward the waist opening part 14 of the panty 10 is clamped by the chuck (the dimensions of the chucking surface is a rectangular of 35 mm×25 mm), the fixing member 20 is extended by 50% at a pulling speed of 100 mm/min. by the tensile tester, and the tensile loads are measured at every 10% of extension.

<Measurement of the Highly Elastic Member>

The highly elastic member 19 of the panty 10 is cut into dimensions of 130 mm in length×25 mm in width. Then, the cut strip is clamped by the chuck (the dimensions of the chucking surface is a rectangular of 35 mm×25 mm), the highly elastic member 19 is extended by 50% at a pulling speed of 100 mm/min. by the tensile tester, and the tensile loads are measured at every 10% of extension.

The elastic coefficient is a value obtained by dividing the tensile loads measured in the methods described above by the corresponding extension rate. For example, the elastic coefficient in the case where the tensile load is 10 N when extended by 20% is 10 N/0.2=50 N.

Figure 13:
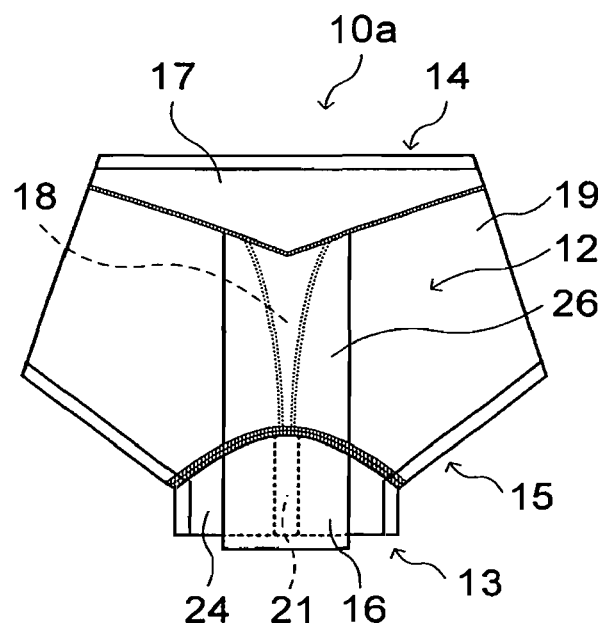
FIG. 13 is a back view showing a second embodiment of a panty according to the present invention, which is shown in a state in which the panty is inside out and folded into two so that the front part and the back part come into contact with each other.
Figure 14:
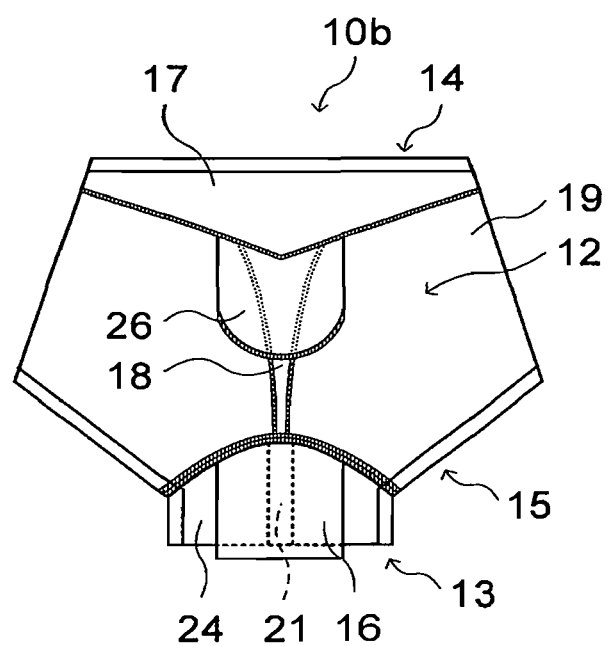
FIG. 14 is a back view showing a third embodiment of a panty according to the present invention, which is shown in a state in which the panty is inside out and folded into to so that the front part and the back part come into contact with each other.

Referring next to FIG. 13 and FIG. 14, the panty 10a according to the second embodiment and the panty 10b according to the third embodiment of the present invention will be described. FIG. 13 is a back view showing the panty 10a according to the second embodiment in the state of inside out and being folded into two so that the front part and the back part come into contact with each other. FIG. 14 is a back view of another form of the second embodiment shown in FIG. 13. In this embodiment, the identical components as the first embodiment are represented by the identical reference numerals, and the redundant description is omitted.

The panty 10a of the second embodiment shown in FIG. 13 is a panty which is different from the panty 10 of the first embodiment in that a waterproof cloth 26 with the width of 30 to 140 mm, more preferably in the order of 80 mm is provided inside of the panty 10a at the substantially center area of the back part 12, which extends from the crotch part 13 to the waist hold part 17. The waterproof cloth 26 is stitched on the crotch part 13, the waist hold part 17, and the slightly elastic member 18 so as to be integral with the main body of the panty 10a. The left and the right ends of the waterproof cloth 26 are left free without being stitched on the back part 12 of the panty 10a so as not to inhibit the stretching property of the panty 10a.

The waterproof cloth 26 is, as in the case of the napkin fitting cloth 16 described above, a cloth-film integration formed by stitching a waterproof cloth formed of polyurethane-laminated polyester circular dappled knit and polyester knitted fabric for protecting the laminated film surface together around the left and right ends. The waterproof cloth 26 has such elasticity in the longitudinal and lateral directions to the extent that does not impair the elasticity of the main body of the panty 10a.

By providing the waterproof cloth 26 in the substantially center area of the back part 12 on the inside of the panty 10a, when menstrual blood is discharged to the amount exceeding the absorbing capacity of the sanitary napkin, the menstrual blood flowing over the sanitary napkin is received by the waterproof cloth 26, and is prevented from leaking outside the panty 10a.

The waterproof cloth 26 may be provided in such a manner in which the lower end of the waterproof cloth 26 does not extend all along to the crotch part 13, but extends from the waist hold part 17 to the substantially midsection of the back part 12. In other word, the waterproof cloth 26 may extend from the waist hold part 17 to the portion which is not covered by the sanitary napkin so that the front end of the sanitary napkin is placed on the waterproof cloth 26 in the worn state. The waterproof cloth 26 is stitched on the waist hold part 17 and the slightly elastic member 18, and on the backside highly elastic member 19b of the back part 12 at the lower end thereof so as to be integral with the main body of the panty 10b. The left and right ends of the waterproof cloth 16 are left free without being stitched with the main body of the panty 10b so as not to impair the elastic characteristics of the main body of the panty 10b.

Figure 15:
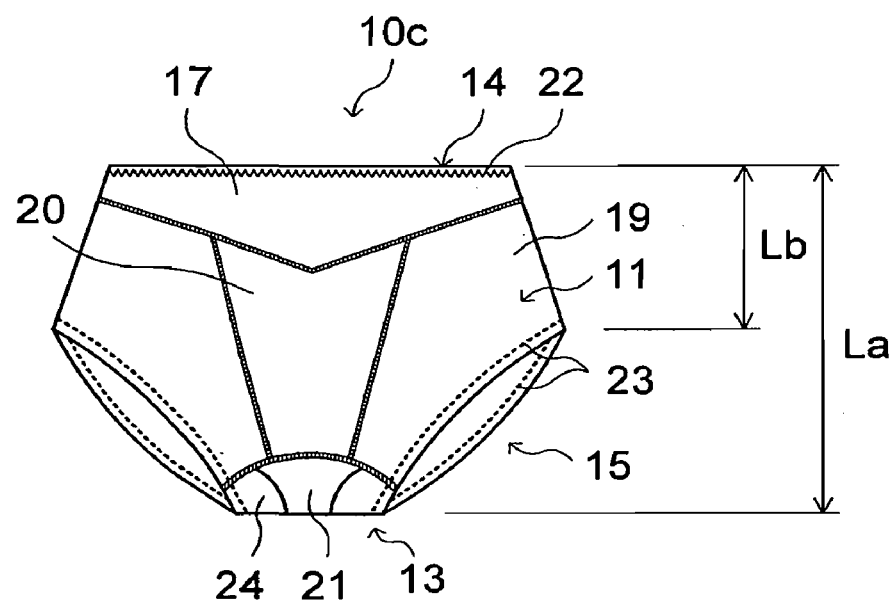
FIG. 15A is a front view showing a fourth embodiment of a panty according to the present invention, which is shown in a state in which the panty is folded into to so that the front part and the back part come into contact with each other.
FIG. 15B is a back view showing the panty according to the fourth embodiment, which is shown in a state in which the panty is folded into two so that the front part and the back part come into contact with each other.
Figure 15:
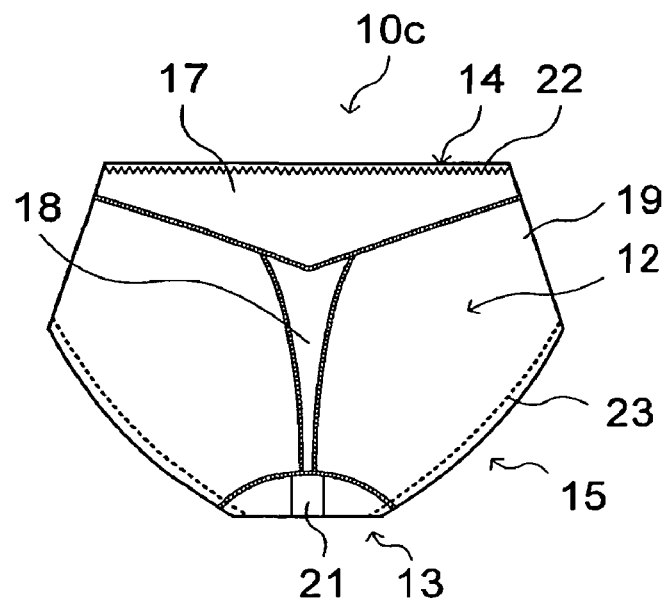

Referring next to FIG. 15, the fourth embodiment of the present invention will be described. FIG. 15 is a drawing of the panty according to the fourth embodiment of the present invention, showing the state of being folded into two so that the front part and the back part come into contact with each other in the not-worn condition. FIG. 15A is a front view showing the state of being folded into two, and FIG. 15B is a back view of the state of being folded into two. In this embodiment, the identical components as the first to the third embodiments are represented by the identical reference numerals, and the redundant description is omitted.

The panty 10c according to the fourth embodiment shown in FIG. 15A and FIG. 15B has a similar structure to the panty 10 in the first embodiment other than that the dimensional ratio between the center height length La from the crotch part 13 to the waist opening part 14 and the side height length Lb of the shortest portion between the leg openings 15 to the waist opening part 14 is set at 100 for the length La and between 50 and 80 at the Lb. The panty 10c is, being different from the panty 10 of the first embodiment, not in the shape of the boxer shorts, and thus is compact and the center height length from the crotch part to the waist opening part is shorter than the side height length of the shortest portion between the leg openings and the waist opening part. The panty 10c may be provided with the waterproof cloth 26 shown in FIG. 13 and FIG. 14 at the substantially center area of the back part 12 of the panty 10c on the inside thereof.

Figure 16:
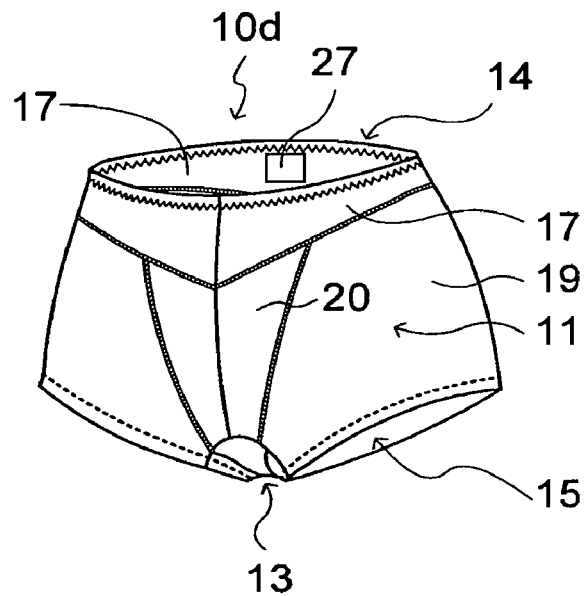
FIG. 16A is a three dimensional perspective view showing a fifth embodiment of the panty according to the present invention as viewed from the side of the front part.
FIG. 16B is a three dimensional perspective view showing the panty according to the embodiment as viewed from the side of the back part.
Figure 16:
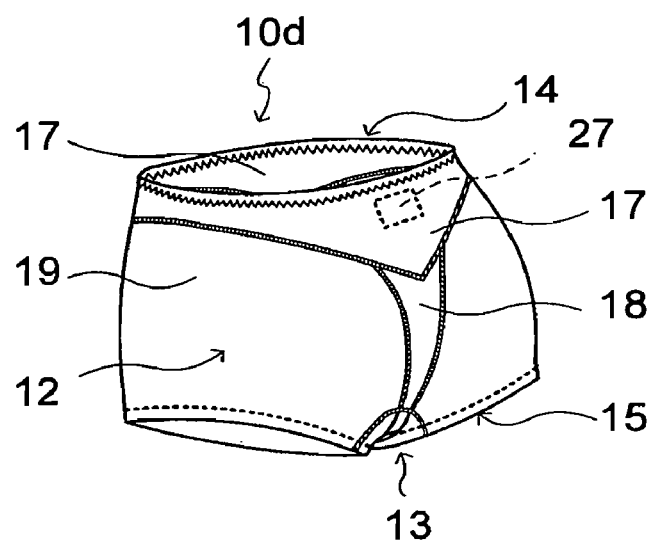
Figure 17:
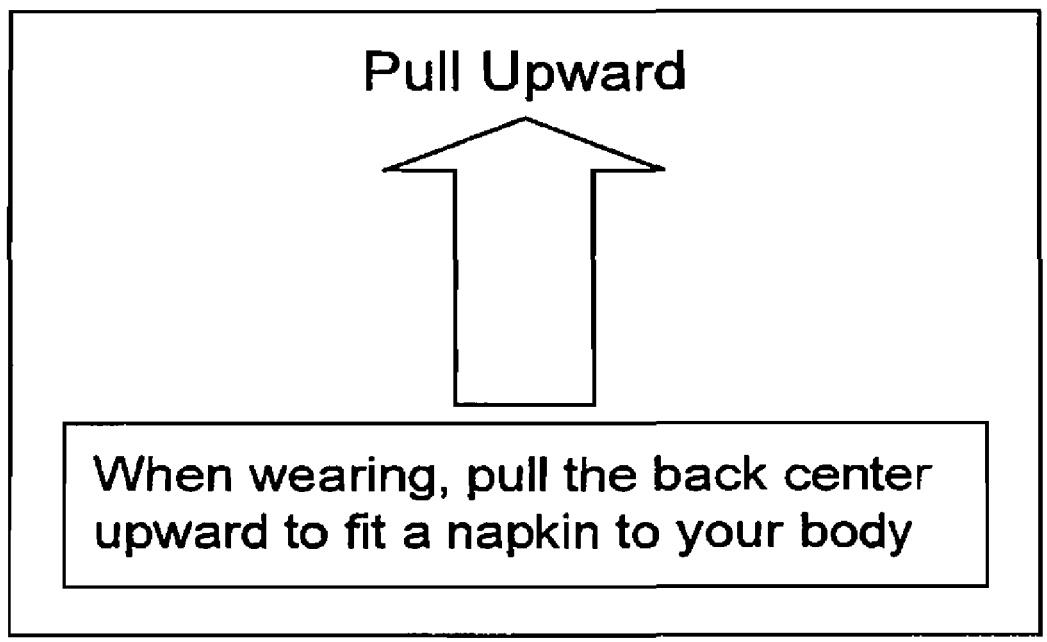
FIG. 17 is an enlarged view of an instruction provided on the panty according to the embodiment.

Referring next to FIG. 16A, FIG. 16B and FIG. 17, a fifth embodiment of the present embodiment will be described. FIG. 16A and FIG. 16B are perspective views showing the panty according to the fifth embodiment three-dimensionally. FIG. 16A is a perspective view viewed from the side of the front part 11, and FIG. 16B is a perspective view viewed from the side of the back part 12. FIG. 17 is an enlarged view of an instruction provided on the panty according to the fifth embodiment. In this embodiment, the identical components as the first embodiment are represented by the identical reference numerals, and the redundant description is omitted.

The panty 10c according to the fifth embodiment shown in FIG. 15 has a similar structure to the panty 10 in the first embodiment other than the instruction 27 is provided inside of the panty 10d at the position in the vicinity of the waist opening part 14 above the extension line of the slightly elastic member 18 provided in the substantially center area of the back part 12. The instruction 27 is a tag showing the preferable way of use of the panty, and is stitched to the panty 10d at the position described above, as shown in FIG. 17.

Accordingly, when the wearer attaches the sanitary napkin to the napkin fitting cloth 16 (not shown) of the panty 10d via an adhesive agent or the like and pulls the panty 10d to the prescribed position of the body for wearing, the wearer, who desires higher adhesion of the sanitary napkin, can obtain the adhesion of her preference by pulling the panty 10d upward by holding the side portions thereof and then further pulling the panty by holding the tag of the instruction 27.

Though the instruction 27 in this embodiment is formed by stitching the tag indicating how to wear, it is not limited thereto, and may be those provided clearly by print or by embroidery yarn. Alternatively, it may be indicated with a laundry tag. The position to provide the instruction 27 is also not limited to the position described above, and may be determined as appropriate depending on the contents of instruction of how to wear. It is also possible to provide on the exterior side of the panty 10d. The contents of the instruction are also not limited to the example described above.

Although the panty according to the present invention has been described in detail referring to the illustrative drawings, the present invention originally is not limited to those illustrative drawings, and may be implemented by modifying to the extent without departing the scope described above, and those modifications are included in the technological scope of the present invention.

As described thus far, the panty according to the present invention realizes easy fit of the thick sanitary napkin for night use to the crotch portion or to the gluteal cleft, and may prevent shifting out of position, and in addition, the present invention may alleviate digging into the crotch portion and thus is comfortable to wear without constricting entirely as in the case of a girdle. In other words, since the slightly elastic member and the napkin lifting part lift up the center portion of the sanitary napkin for night use from the portion corresponding to the ostium vagina and the back parts to fit it to the body, the gap, which may cause leakage by flowing down through, is eliminated, so that the sanitary napkin is reliably fitted to the body irrespective of the posture of the wearer. As a consequence, the cause of leakage of menstrual blood by flowing along the gluteal cleft may be eliminated, and thus the wearer can sleep in any posture at ease and can wake up feeling entirely refreshed. In addition, since the area of spread of menstrual blood is small, the area of the skin to which menstrual blood comes in contact is narrowed and hence stimulus to the skin is reduced and, consequently, skin irritation and the like is prevented.

Further, since the surrounding highly elastic member other than the slightly elastic member and the surrounding crotch cloth other than the napkin lifting part are formed of cloth which has high elasticity and high air permeability, it does not cause the excessive uncomfortable feeling of constriction, and swelling or hematogenous disorder due to tightness. Therefore, it does not give stress to the body, and does not cause the uncomfortable feeling of constriction even after long time use.

In addition, since the belly portion (front part) is controlled by the fixing member formed of a power net, the panty is prevented from slipping down and the sanitary napkin is firmly fixed.

What is claimed is:

1. A panty comprising:
   a front part;
   a back part;
   a crotch part provided so as to bridge between the front part and the back part, the crotch part being utilized for fitting a sanitary napkin, said crotch part including a crotch cloth;
   a waist opening part provided in an upper edge of the front part and an upper edge of the back part;
   a pair of leg openings provided below both side edges of the front part and both side edges of the back part; and
   a napkin lifting part provided in a middle of the crotch cloth and extends in a longitudinal direction exclusively from and between a front edge of the crotch cloth at a side of the front part to and between a back edge of the crotch cloth at a side of the back part, a width of the napkin lifting part gradually narrows for a distance from the front edge toward the back edge,
   wherein, a longitudinal elastic coefficient of the napkin lifting part is larger than a longitudinal elastic coefficient of the crotch cloth.

2. The panty according to claim 1, wherein the napkin lifting part is formed of a material which is non-elastic in the longitudinal direction.

3. The panty according to claim 1, further comprising an elastic member provided at the substantially center area of the back part, wherein the longitudinal elastic coefficient of the napkin lifting part is smaller than the longitudinal elastic coefficient of the elastic member.

4. The panty according to claim 3, wherein a width of the elastic member gradually narrows for a distance from the waist opening part at the back part toward the napkin lifting part.

5. The panty according to claim 4, wherein the width of the elastic member gradually narrows along a major portion of a longitudinal length thereof.

6. The panty according to claim 1, wherein the width of the napkin lifting part ranges between 20 mm and 60 mm.

7. The panty according to claim 1, further comprising a fixing member provided at a substantially center area of the front part, wherein the longitudinal elastic coefficient of the fixing member is larger than the longitudinal elastic coefficient of front part.

8. The panty according to claim 7, wherein the fixing member is generally V-shaped so as to gradually narrow from the waist opening part to the crotch part.

* * * * *